United States Patent
Kouyoumjian et al.

(10) Patent No.: US 9,180,255 B2
(45) Date of Patent: Nov. 10, 2015

(54) RESETTABLE DRIVE ASSEMBLY AND DRUG DELIVERY DEVICE

(75) Inventors: Garen Kouyoumjian, Leamington Spa (GB); Robert Veasey, Leamington Spa (GB); David Plumptre, Droitwich Spa (GB); Christopher Jones, Tewkesbury (GB); Catherine Anne MacDonald, Ashby-de-la-Zouch (GB); James May, Kenilworth (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 575 days.

(21) Appl. No.: 13/498,220

(22) PCT Filed: Sep. 29, 2010

(86) PCT No.: PCT/EP2010/064429
§ 371 (c)(1),
(2), (4) Date: Jul. 31, 2012

(87) PCT Pub. No.: WO2011/039236
PCT Pub. Date: Apr. 7, 2011

(65) Prior Publication Data
US 2012/0289908 A1    Nov. 15, 2012

(30) Foreign Application Priority Data

Sep. 30, 2009    (EP) .................................. 09171767

(51) Int. Cl.
*A61M 5/315*    (2006.01)
*A61M 5/31*    (2006.01)
*A61M 5/24*    (2006.01)

(52) U.S. Cl.
CPC ......... *A61M 5/31543* (2013.01); *A61M 5/3156* (2013.01); *A61M 5/3157* (2013.01);

(Continued)

(58) Field of Classification Search
CPC ..................... A61M 5/31543; A61M 5/31551; A61M 5/3158; A61M 5/3151
USPC .................................................. 604/207–211
See application file for complete search history.

(56) References Cited

U.S. PATENT DOCUMENTS 7,704,238 B2 *    4/2010    Diller et al. .................... 604/224
2005/0033244 A1 *    2/2005    Veasey et al. ................. 604/211

(Continued)

FOREIGN PATENT DOCUMENTS

| AU | 2007201751 A1 | 5/2007 |
| EP | 1923083 A1 | 5/2008 |
| EP | 1923084 A1 | 5/2008 |
| EP | 1923085 A1 | 5/2008 |

(Continued)

OTHER PUBLICATIONS

Form PCT/IB/308, Notification Concerning Transmittal of International Preliminary Report on Patentability.

*Primary Examiner* — Theodore Stigell
*Assistant Examiner* — Benjamin Koo
(74) *Attorney, Agent, or Firm* — McDonnell Boehnen Hulbert & Berghoff LLP

(57) ABSTRACT

A resettable drive assembly for a drug delivery device (1) is provided. The drive assembly comprises a drive unit (3) for driving a piston rod (5) in a dispense operation of the device (1). The drive unit (3) comprises a first drive member (35), a second drive member (37) and locking means preventing a relative rotational movement of the first (35) and the second drive member (37) during a dispense operation and allowing a relative rotational movement for enabling a resetting of the device (1). Moreover, a drug delivery device (1) comprising a resettable drive assembly is provided.

15 Claims, 8 Drawing Sheets

Figure 1A:
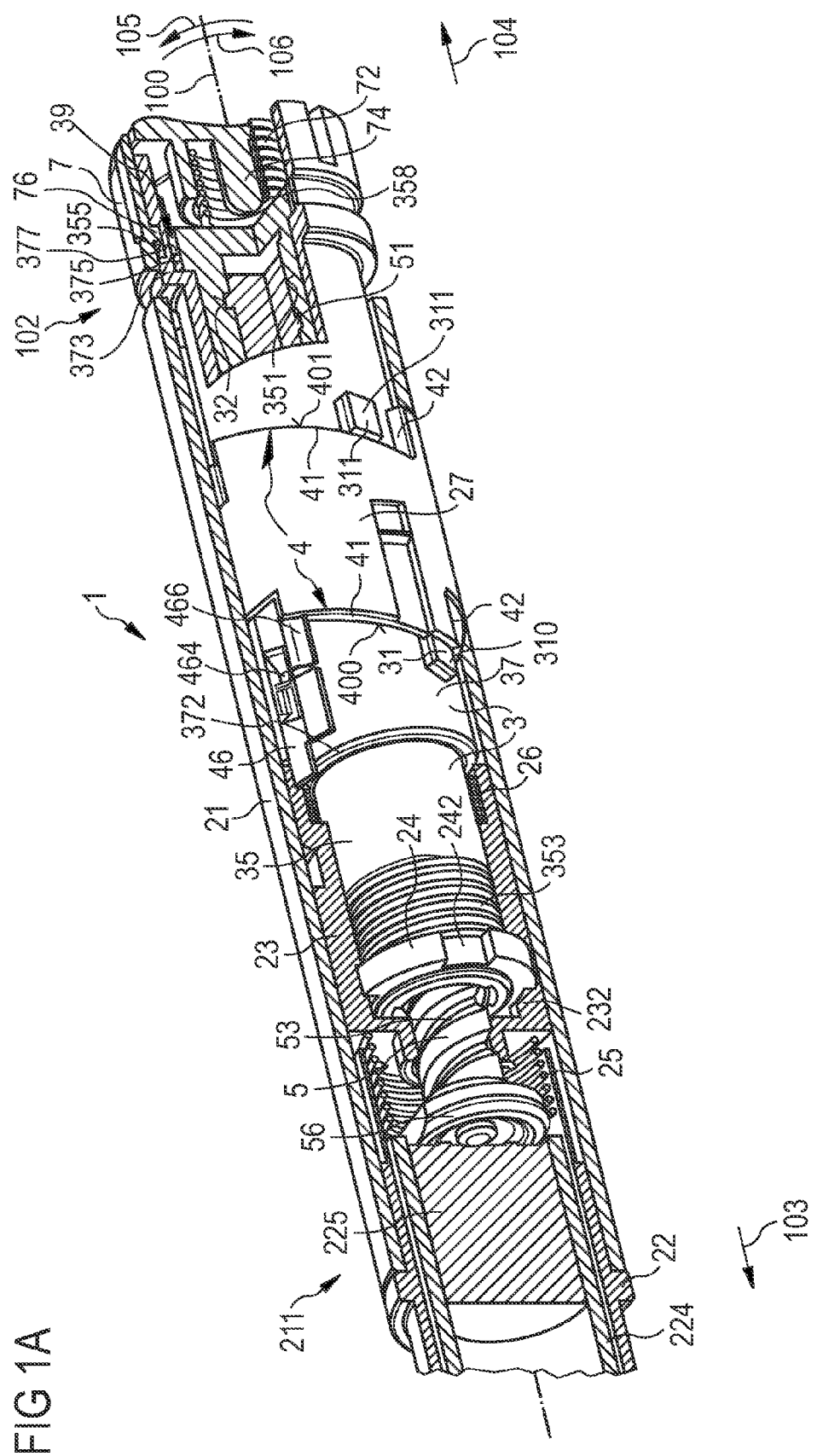

(52) U.S. Cl.
CPC ......... *A61M5/3158* (2013.01); *A61M 5/31551* (2013.01); *A61M 5/3135* (2013.01); *A61M 5/3146* (2013.01); *A61M 5/31511* (2013.01); *A61M 5/31535* (2013.01); *A61M 5/31568* (2013.01); *A61M 5/31575* (2013.01); *A61M 2005/2407* (2013.01); *A61M 2005/2488* (2013.01); *A61M 2005/3103* (2013.01); *A61M 2005/3126* (2013.01); *A61M 2005/31508* (2013.01); *A61M 2005/31518* (2013.01); *A61M 2205/581* (2013.01); *A61M 2205/582* (2013.01)

(56) References Cited

U.S. PATENT DOCUMENTS

2008/0287883 A1 11/2008 Radmer et al.
2009/0275914 A1* 11/2009 Harms et al. .................. 604/506

FOREIGN PATENT DOCUMENTS

WO 2006024461 A1 3/2006
WO 2008058665 A1 5/2008

* cited by examiner

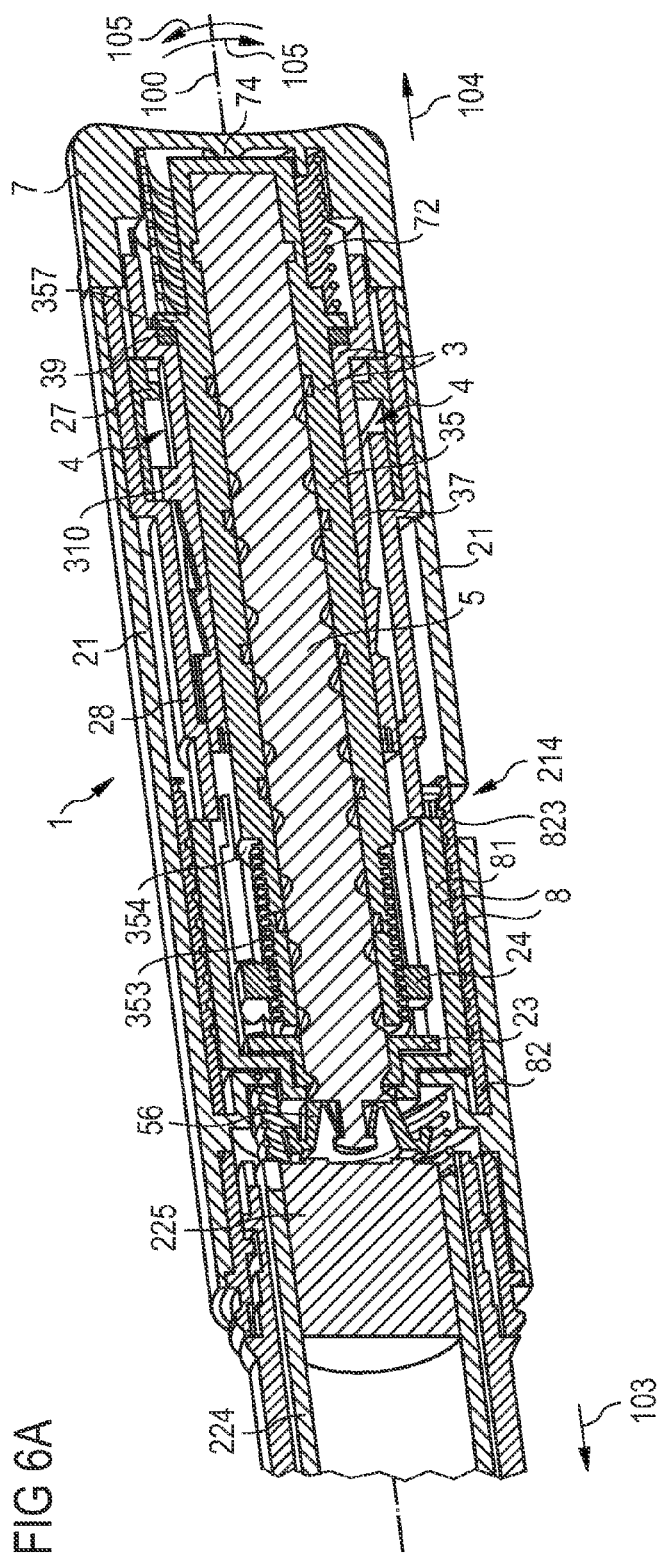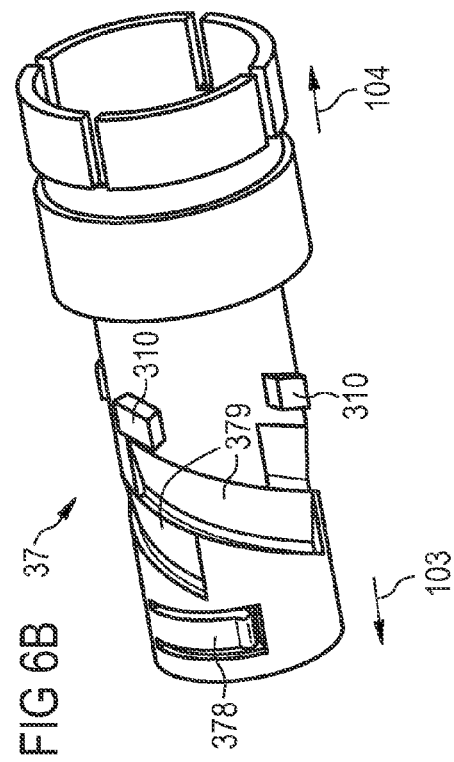

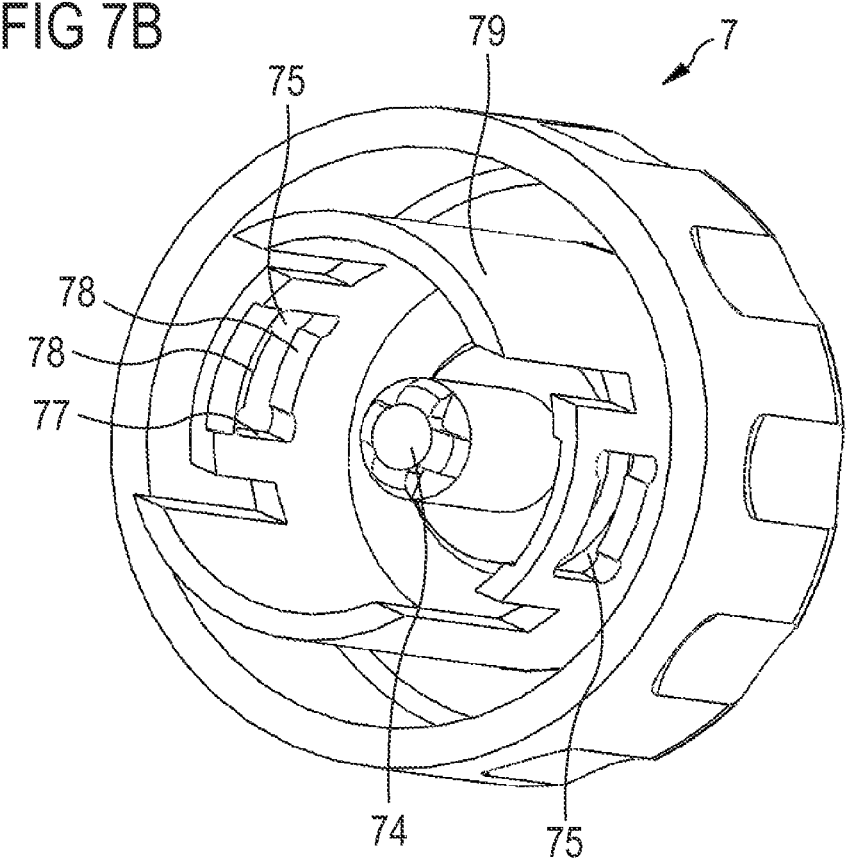

RESETTABLE DRIVE ASSEMBLY AND DRUG DELIVERY DEVICE

CROSS REFERENCE TO RELATED APPLICATIONS

The present application is a 35 U.S.C. 371 National Application of PCT/EP2010/064429 filed Sep. 29, 2010, which claims priority to European Patent Application No. 09171767.8, filed Sep. 30, 2009, the entire contents of which are incorporated entirely herein by reference.

This disclosure relates to a drive assembly suitable for driving a piston rod in a drug delivery device for dispensing one or more doses of a drug. In particular, it relates to a resettable drive assembly which enables a piston rod to be reset to an initial position. Moreover, it relates to a drug delivery device comprising such a resettable drive assembly. In particular, the drug delivery device may be a reusable pen-type injector.

The European patent applications EP 1 923 083 A1, EP 1 923 084 A1, EP 1 923 085 A1 and the international patent application WO 2008/058665 A1 disclose drug delivery devices, wherein a number of pre-set doses of a medicinal product can be administered.

It is the aim of the present invention to provide a drive assembly and a drug delivery device enabling a user-friendly and robust resetting.

According to a first aspect, a resettable drive assembly for use in a drug delivery device is disclosed. The drive assembly comprises a drive unit for driving a piston rod in a dispense operation of the drug delivery device.

Preferably, the drive unit is configured for directly acting on the piston rod, thereby causing a movement of the piston rod in a distal direction of the device. Preferably, in an assembled state of a drug delivery device comprising the drive unit the distal direction points to the dispensing end of the device. The proximal direction is the direction opposite to the distal direction. In the following, the terms "distal end" and "proximal end" of a component usable in a drug delivery device denote the ends of the component which are reached when moving from the center of the component in the distal or the proximal direction, respectively.

A piston rod is a component of a drug delivery device, which, by carrying out a movement in the distal direction of the drug delivery device, causes medicament to be dispensed from the device. In particular, the piston rod may push a bung in a cartridge containing the medicament in the distal direction. The piston rod may be configured for carrying out a combined axial and rotational movement. As an example, the piston rod may be a simple rod or a lead-screw having threads for engaging with corresponding parts of the drug delivery device. The piston rod may be of a unitary or a multi-part construction. The piston rod may be threadedly engaged with a nut, which may be fixed to a housing of the device.

Preferably, the resettable drive assembly is configured such that a resetting of the piston rod towards an initial position is allowed. Thereby, a reuse of a drug delivery device with different medicament containers may be enabled.

For this aim, the drive unit comprises a first drive member and a second drive member, wherein during a dispense operation, the first and second drive member are locked to each other such that a relative rotational movement is prevented and wherein during a reset operation a relative rotational movement is allowed. In particular, the drive assembly may comprise locking means configured to rotationally lock the first and second drive member in a dispense operation and configured to allow unlocking for enabling a resetting of the piston rod. Preferably, the unlocking takes place during the reset operation.

As an example, the first and the second drive member may have the shape of sleeves extending along a longitudinal axis. Preferably, the first drive member is at least partly positioned within the second drive member. In an assembled state of the device, the piston rod may be partly positioned within the first drive member.

The second drive member may be configured for coupling the drive unit to a housing of a drug delivery device such that a dispense operation is enabled. As an example, at its outer surface, the second drive member may have engaging features, for example protrusions, which are guided in a track at an inner surface of the housing of the device. Preferably, the second drive member is permanently coupled to the housing, for example both during set, dispense and reset operations. In this context, a "set operation" and "setting a dose" means that the drive mechanism is prepared for a subsequent dose dispense operation.

The first drive member may be configured for coupling the drive unit to a piston rod, thereby enabling driving the piston rod in a dispense operation. As an example, at its inner surface the first drive member may comprise coupling means, for example a thread, wherein a protrusion of the piston rod is engaged.

In a preferred embodiment, the locking means are configured to unlock the first and second drive member by exerting a load onto the first drive member in a proximal direction of the drive unit.

This enables a simple and user-friendly resetting of the device. In particular, here, applying an axial load on the piston rod in the proximal direction may be the only action needed for resetting the piston rod in a drug delivery device.

In particular, in a drug delivery device, the piston rod may be coupled to the first drive member such that an axial load on the piston rod results in an axial load on the first drive member. In the case that the second drive member is coupled to the housing such that an axial movement of the second drive member is prevented, the axial load of the piston rod may result in a small displacement of the first drive member from the second drive member, whereby an unlocking of the first and second drive member may be achieved.

In one embodiment, the locking means comprise clutch means for rotationally coupling the first drive member and the second drive member. As an example, the clutch means may be configured as teeth on the first drive member and matching teeth on the second drive member engaged with each other in a dispense operation. In particular, the clutch means may be located at the proximal ends of the first and the second drive member. Preferably, the clutch means are configured to be disengaged by an axial movement of the first drive member in the proximal direction relative to the second drive member.

Moreover, the locking means may comprise biasing means configured to maintain the first and the second drive member in their locked state in a dispense operation of the drug delivery device.

In particular, the biasing means may maintain a clutched engagement of the first and the second drive member. As an example, the biasing means may comprise a spring exerting a load onto one of the first drive member and the second drive member.

Preferably, at least in an assembled state of the drug delivery device, the biasing means push the first and the second drive member towards each other such that the clutch means are maintained in or urged in their clutched engagement.

Preferably, the biasing means are configured such that on exerting a sufficiently high load on the first drive member in the proximal direction, a rotational unlocking of the first and the second drive member is achieved. As an example, on applying an axial load on the first drive member in the proximal direction, a spring of the biasing means may be compressed, whereby a movement of the first drive member relative to the second drive member is enabled.

In one embodiment, the locking means are configured such that also in a set operation of the drug delivery device a relative rotational movement between the first drive member and the second drive member is prevented. Furthermore, the locking means may be configured such that also a relative translational movement of the first and the second drive member is prevented in one of or both a dose set and dose dispense operation.

In one embodiment, the device is configured such that during a dose set operation the first and second drive members rotate relative to a housing of the device, for example, carry out a helical movement relative to the housing. Thereby, during a dose set operation, the first and second drive members may rotate relative to a nut which may be threadedly engaged with a piston rod. Furthermore, the device may be configured such that during a dose dispense operation the first and second drive members carry out an axial movement relative to the housing, for example, a purely axial movement. Thereby, during a dose dispense operation, the first and second drive members may move axially relative to a nut which may be threadedly engaged with a piston rod.

In a second aspect of the present disclosure, a drug delivery device comprising such a resettable drive assembly is provided. The drug delivery device comprises a piston rod configured to be driven by the drive unit for dispensing a dose of a medicament. The drug delivery device is configured such that, for resetting the device, the piston rod is movable towards an initial position.

Preferably, for dispensing the medicament, the piston rod acts on a bung in a medicament cartridge and pushes the bung in the distal direction. Thereby, during dispense of the medicament, the piston rod moves in the distal direction. In order to enable reusing the device with a new cartridge, the piston rod has to be moved back in the proximal direction.

As an example, after the last dose of medicament has been dispensed, the empty cartridge can be replaced by a full cartridge. Moreover, a user may choose to replace a cartridge containing an expired medicament.

The drug delivery device may comprise a main housing to which a cartridge holder containing a medicament cartridge can be releasably attached. Preferably, in order to replace a cartridge, the cartridge holder is removed from the main housing, allowing the piston rod to be accessed from the outside and to be moved back into its initial position. After that, the cartridge holder comprising a new cartridge can be attached to the main housing.

The piston rod may be threadedly engaged with the housing or a component fixed to the housing. In this case, for resetting the piston rod, the piston rod may be pushed or rotated backwards. In both cases, the piston rod rotates through its threaded engagement with the housing or the component fixed to the housing and moves in the proximal direction.

Preferably, the drug delivery device is a fixed-dose device. Here, the term "fixed-dose" means that in such a drug delivery device, the user does not have the option of varying the absolute size of a dose. Preferably, the absolute size of a dose to be dispensed is predetermined by the design of the drive mechanism of the drug delivery device and, in particular, may be determined by the design of the drive unit.

The second drive member may be configured such that a free rotational movement of the second drive member relative to a housing of the device is prevented in one rotational direction around a longitudinal axis of the housing.

The piston rod may be coupled to the first drive member such that a free rotational movement of the first drive member relative to the housing in one rotational direction may be necessary for enabling the resetting of the piston rod. As an example, the piston rod may be threadedly engaged with the first drive member.

In the case that a free rotational movement of the second drive member relative to the housing is prevented in the relevant rotational direction, a resetting may be enabled by rotationally unlocking the first and the second drive member.

As an example, the second drive member and the housing may be moveable relative to each other only along a pre-defined track on one of the second drive member and the housing or a component fixed to the housing.

In particular, the second drive member, the housing or a component fixed to the housing may comprise protrusions guided along the track. Thereby, the movement of the second drive member relative to the housing is restricted to a movement of the protrusions along the track. Such a track may comprise both sections running in the distal direction and sections running in the proximal direction of the drug delivery device. This means that, when following the track in one direction relative to the track, at specific sections of the track, the direction of the movement along the track at least partially points into the proximal direction or into the distal direction of the housing, respectively. The track may comprise stop faces, for example ramped sections, such that a relative movement of the second drive member in a first direction along the track is allowed and a movement in the opposite direction along the track is prevented.

The drug delivery device may comprise a dose member operable by a user to control a set and a dispense operation of the drug delivery device.

Preferably, the dose member is coupled to the second drive member such that a relative rotational movement of the dose member and the second drive member is prevented. Furthermore, the dose member may be coupled to the second drive member such that a limited axial movement between the dose member and the second drive member is enabled. Preferably, the allowed axial movement is small and, in particular, much smaller than an axial movement required for a dose set or dose dispense operation.

The dose member may be located at the proximal end of the drug delivery device and may be configured as a dose button protruding out of the main housing of the device.

The drug delivery device may be configured as a twist-push device such that for setting a dose, the dose member is rotated relative to the housing and thereby carries out a helical movement out of the housing. Here, when the first drive member is rotationally locked to the second drive member during the set operation, the helical movement of the dose member results in a helical movement of the drive unit relative to the housing. For dispensing a dose, the dose member is pushed towards the housing, causing also a movement of the drive unit in the distal direction.

In particular, the dose member may comprise or act on biasing means maintaining a clutched engagement of the first and the second drive member during a dose dispense operation. In particular, a spring may be located at the dose member, pushing the first and second drive member towards each other. During resetting the device, an axial load on the first drive member may further compress the spring such that the first drive member is moveable in the proximal direction relative to the second drive member. Thereby, the first and the second drive member may come out of their clutched engagement allowing a relative rotational movement needed for resetting the piston rod.

Furthermore, the dose member may be configured such that on exerting a load on the dose member in the distal direction, the dose member exerts a load onto one of the first and the second drive member, thereby maintaining the first and the second drive member in their locked state in a dispense operation of the device.

As an example, the biasing means may comprise a rigid part which presses the first and second drive member towards each other when the dose member is pushed in the distal direction for dispensing a dose. Preferably, the rigid part directly acts on the first drive member.

In particular, the dose member may comprise a boss acting on one of the first and second drive member during a dose dispense operation, thereby maintaining their clutched engagement. For this aim, a limited axial movement of the dose member relative to the second drive member may be enabled, enabling the boss to interact with the first drive member during a dose dispense operation.

In order to enable the limited axial movement of the dose member relative to the second drive member, one of the dose member and the second drive member may comprise a protrusion being guided in a short axial groove at the other one of the drive member and the dose member. In this case, the second drive member and the dose member are allowed to carry out a small relative axial movement to each other. By such an axial movement, a spring located in the dose member may be compressed until the boss acts on a proximal face of the first drive member. Thereby, the locked state is also maintained in the dose dispense operation, when the drive unit is pushed in the distal direction against a counterforce exerted by the bung in a cartridge.

Furthermore, such a boss may form a counter-bearing for the first drive member during resetting the piston rod. In particular, here, a load in the proximal direction applied on the first drive member may cause a compression of the spring such that the boss comes into contact with the proximal face of the first drive member. Thereby, the axial movement of the first drive member during resetting is constrained and a rotational movement is facilitated.

Preferably, the drug delivery device is configured to be resettable by exerting a force on the piston rod in the proximal direction. Thereby, the locking means are unlocked such that a rotational movement between the first drive member relative to the second drive member is enabled. This enables the piston rod to be moved in the proximal direction of the drug delivery device, whereby the first drive member is rotated relative to the second drive member. When the piston rod has arrived at the initial position the force is removed.

Note here that the piston rod does not have to be manually moved back to its initial position. As an example, the piston rod may be moved in the proximal direction by attaching a cartridge holder containing a cartridge and here, in particular, by a load exerted by the bung in the cartridge.

After removing the axial load from the piston rod, for example by releasing the piston rod, the locking means may automatically rotationally lock the first drive member and the second drive member. As an example, the biasing means may push the first drive member and the second drive member towards each other.

In a further embodiment, the locking means may not immediately lead to a rotational locking of the first and the second drive member. In this case, a small rotational movement of the dose member may be required to establish the rotational locking. As an example, the clutch means of the first and the second drive member may be misaligned when the piston rod is released. In this case, the biasing means urges the first drive member and the second member towards each other such that on a small rotational movement of the dose member and therewith also the second drive member, the clutch means are aligned and rotationally lock the first and second drive member.

Here, a priming operation may establish the locking of the first and second drive member. In this context, the term "priming" may mean that relative displacements of parts of the drive mechanism towards each other due to the reset operation are compensated. In particular, the displacement between the first and the second drive member may be compensated such that the clutch is aligned. In order to prime the device after resetting, a set and dispense operation of the dose member may be carried out, before the first dose is dispensed.

The term "drug", as used herein, preferably means a pharmaceutical formulation containing at least one pharmaceutically active compound,
wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp- Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Other features will become apparent from the following detailed description when considered in conjunction with the accompanying drawings.

Figure 1B:
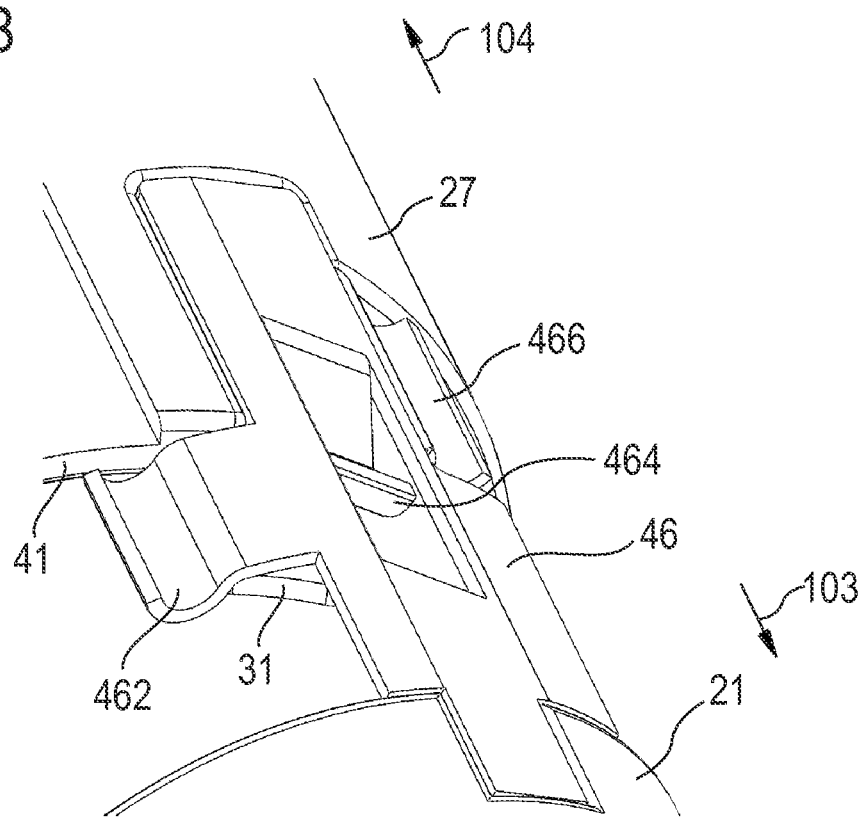
Figure 2A:
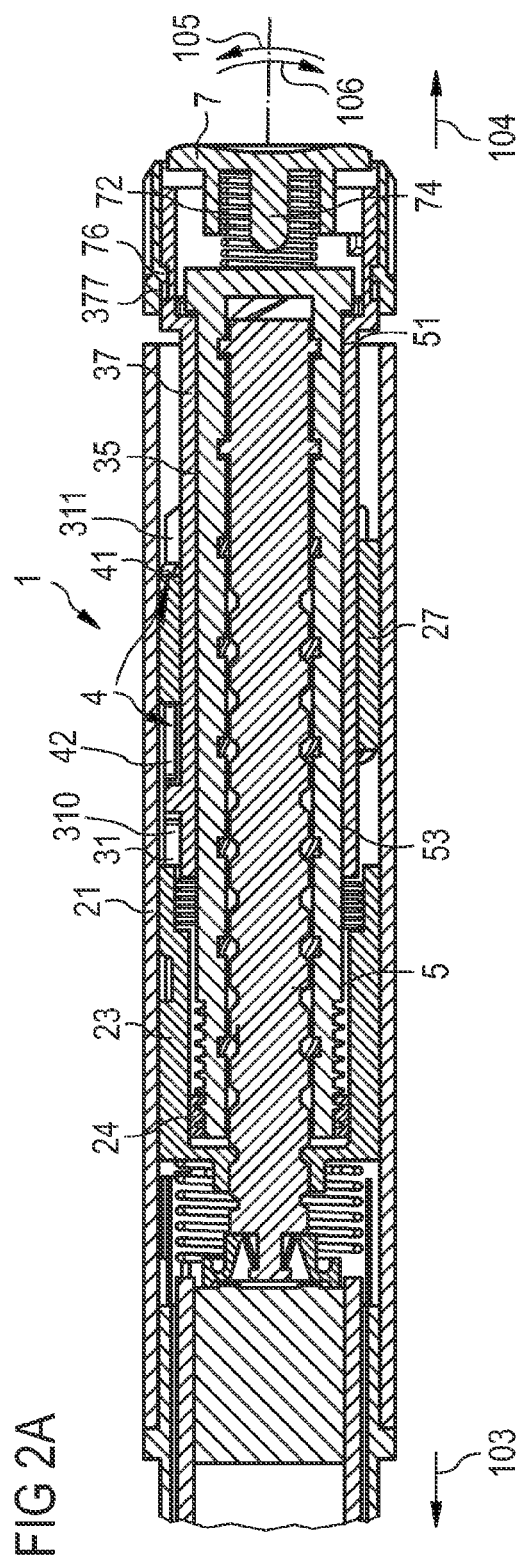
Figure 2B:
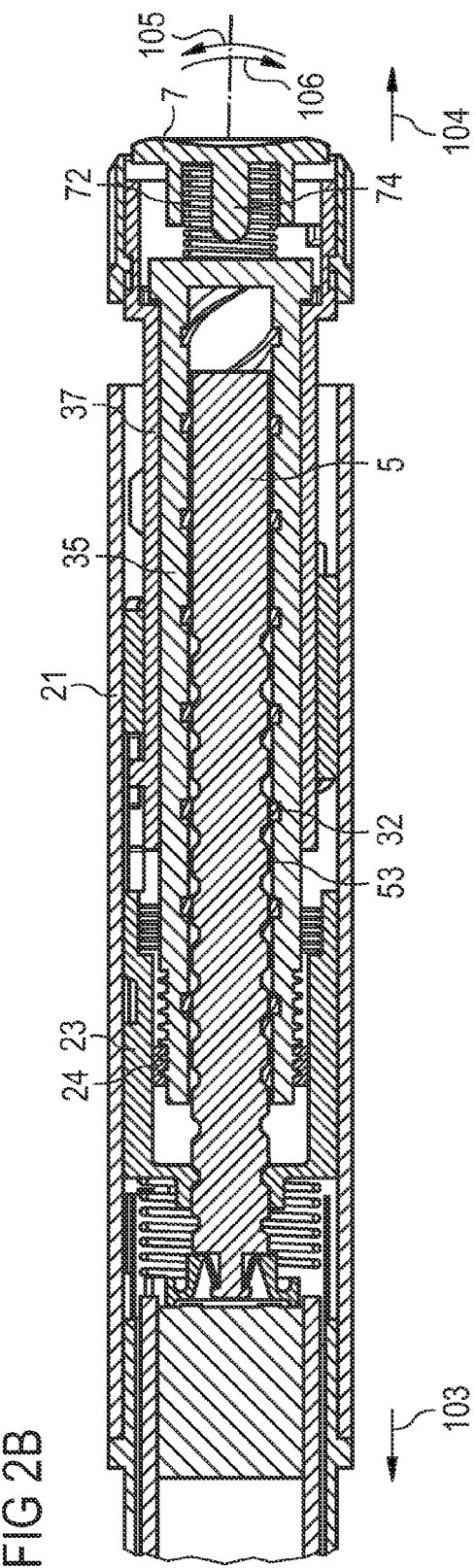
Figure 3:
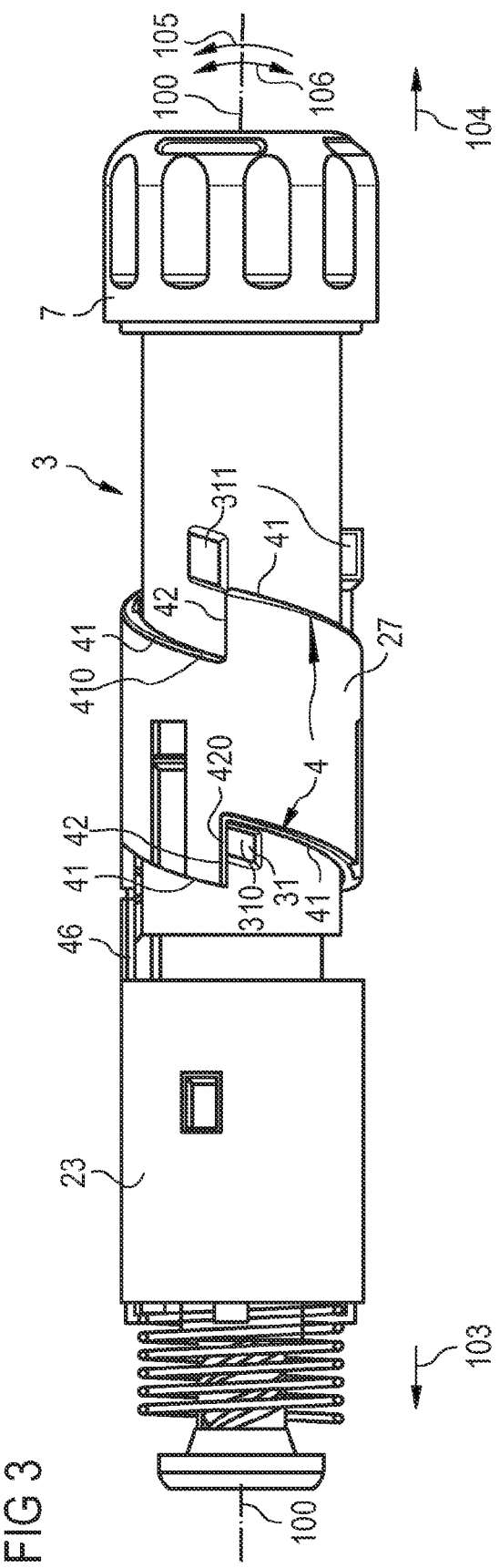
Figure 4:
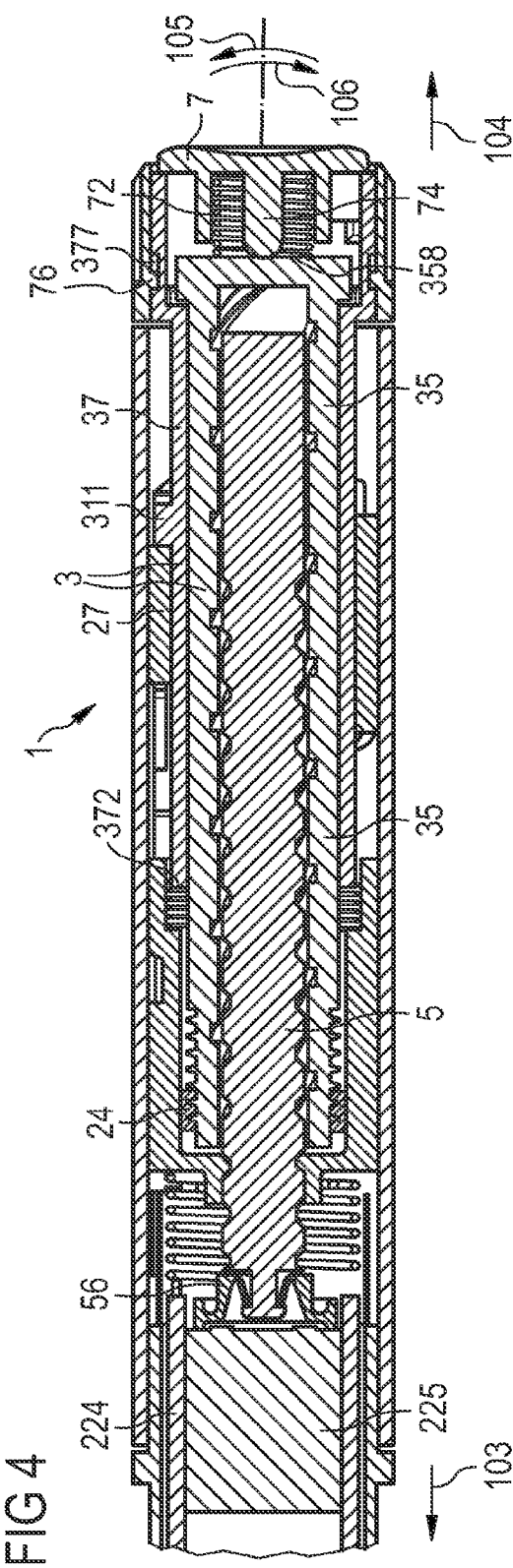
Figure 5:
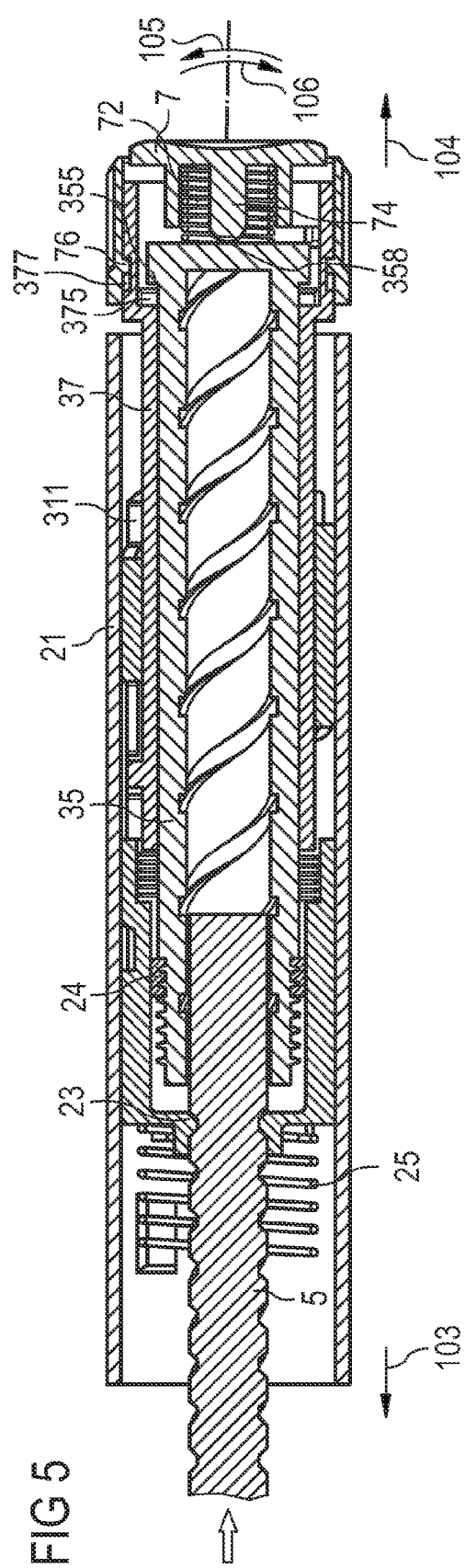
Figure 7A:
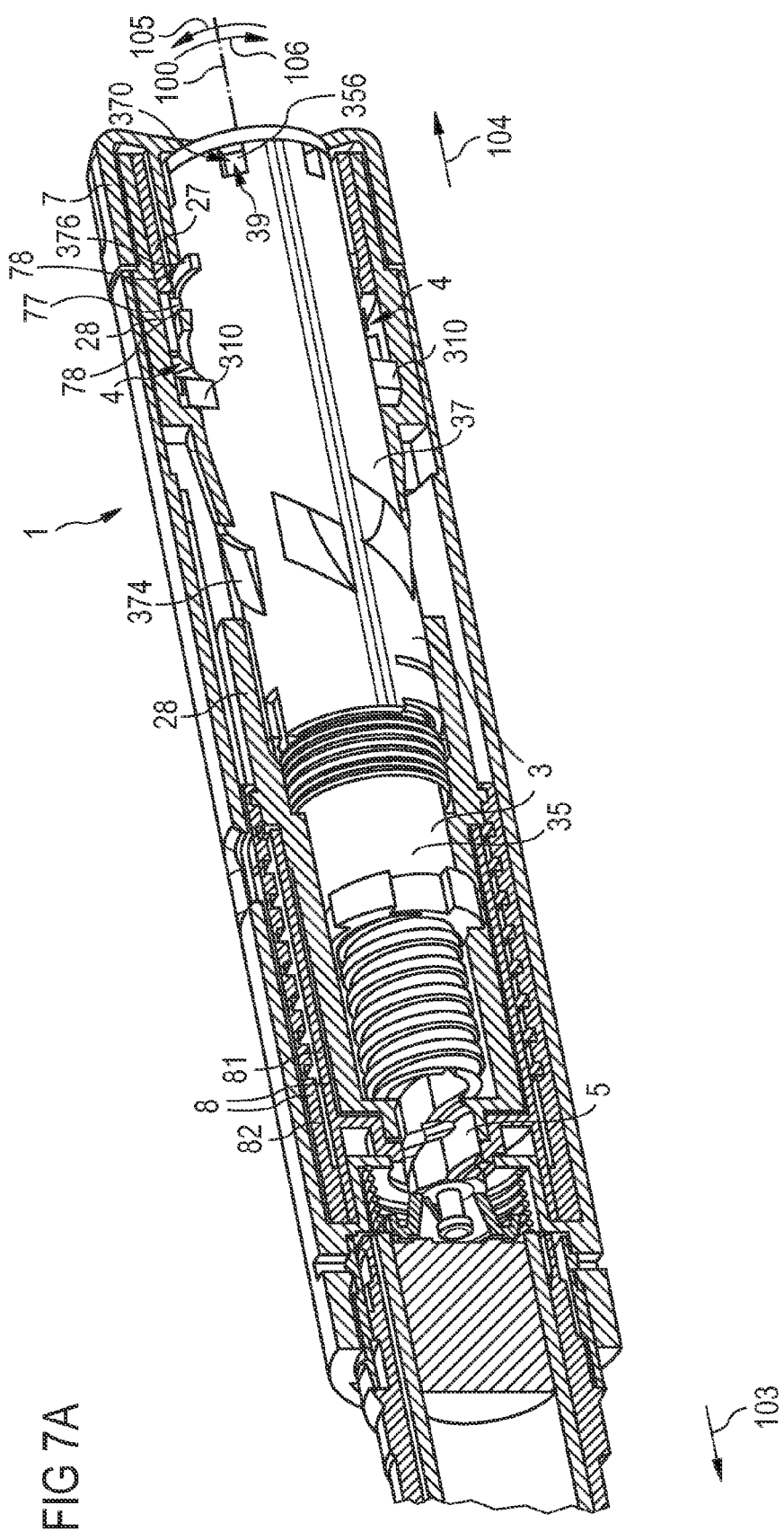

FIG. 1A is a cut-away view of a first embodiment of a drug delivery device,

FIG. 1B is a detailed perspective view of an insert spring of the first embodiment, FIG. 2A is a perspective cross-sectional view of the first embodiment of a drug delivery device before a dose set operation, FIG. 2B is a perspective cross-sectional view of the first embodiment of a drug delivery device during a dose set operation, FIG. 3 is a perspective view of the dispense mechanism of the first embodiment of a drug delivery device during a dose dispense operation, FIG. 4 is a perspective cross-sectional view of the first embodiment of a drug delivery device after a dose dispense operation, FIG. 5 is a perspective cross-sectional view of the first embodiment of a drug delivery device during resetting, FIG. 6A is a perspective cross-sectional view of a second embodiment of a drug delivery device, FIG. 6B is a perspective view of a second drive member of the second embodiment of a drug delivery device, FIG. 7A is a cut-away view of a third embodiment of a drug delivery device, FIG. 7B is a perspective view of a dose member of the third embodiment of a drug delivery device.

FIG. 1A shows a first embodiment of a drug delivery device 1, in particular a pen-type injection device, for setting and dispensing fixed doses of a medicament. The drug delivery device 1 is a reusable multi-dose device allowing subsequent administering of doses from a cartridge 224 and allowing a replacement of the cartridge.

The drug delivery device 1 comprises a main housing 21, which at least partially encloses a drive mechanism of the device 1 and extends along a longitudinal axis 100. At the distal end 211 of the main housing 21, a cartridge holder 22 containing a cartridge 224 filled with a liquid medicament is releasably attached. As examples, the medicament may comprise GLP-1 or heparin. The cartridge holder 22 is screwed onto the main housing 21 of the device 1. In further embodiments, a cartridge holder may have a bayonet connection with a main housing.

When the cartridge holder 22 is attached to the main housing 21, a cartridge bias spring 25 presses the cartridge 224 towards a distal end of the cartridge holder 22. When the cartridge holder 22 is detached from the main housing 21, the cartridge bias spring 25 is released and the empty cartridge 224 can be removed from the cartridge holder 22. After that, a new cartridge 224 can be inserted and the cartridge holder 22 can be reattached to the main housing 21. In a different embodiment, the cartridge holder 22 may be configured to be disposed with the empty cartridge 224 such that for replacing a cartridge 224, a new cartridge holder 22 is attached to the main housing 21.

The cartridge 224 comprises a bung 225 which, for dispensing the medicament, is pushed by a piston rod 5 in the distal direction 103, whereby the medicament is pressed out through a needle (not shown here) at the distal end of the cartridge holder 22. In particular, the piston rod 5 acts on the bung 225 via a bearing 56 located at its distal end. In a dose dispense operation, the piston rod 5 is driven by a drive unit 3 comprising a first 35 and a second drive member 37.

The piston rod 5 has the shape of a double-threaded lead screw extending along the longitudinal axis 100 of the device 1. In particular, the piston rod 5 comprises a female thread 53 running from its distal to its proximal end, engaged with a nut 232 fixed to the main housing 21. Furthermore, at its proximal end, the piston rod 5 comprises a male thread in the form of protrusions 51, threadedly engaged with a female thread 32 on an inner surface of the first drive member 35.

At its proximal end 102, the drug delivery device 1 comprises a dose member 7 operable by a user. The dose member 7 has the shape of a button protruding out of the proximal end of the main housing 21. For setting a dose of the medicament, the dose member 7 is rotated relative to the main housing 21 in a dose set direction 105, whereby the dose member 7 carries out a helical movement out of the main housing 21. For dispensing the set dose, the dose member 7 is pushed in the distal direction 103. If a user, after having set a dose, decides not to dispense the dose, the set dose can be unset by rotating the dose member 7 in a dose unset direction 106 opposite to the dose set direction 105, whereby the dose member 7 carries out a helical movement towards the main housing 21.

The dose member 7 is coupled to the second drive member 37 such that a relative rotational movement of the dose member 7 and the second drive member 37 is prevented and a limited axial movement is allowed. In particular, the dose member 7 comprises a lug 76 being guided in a short axial groove 377 on the outer surface of the second drive member 37. Thereby, a rotational movement during dose setting causes an equivalent movement of the second drive member 37. On an axial movement of the dose member 7 during dose dispense, the dose member first carries out a small axial movement relative to the second drive member 37 until the lug 76 abuts a distal end face of the groove 377. Then, on further pushing the dose member 7 towards the housing 21, the dose member 7 acts on the second drive member 37, thereby pushing the second drive member 37 in the distal direction 103.

The first drive member 35 and the second drive member 37 have the shapes of hollow cylindrical sleeves extending along the longitudinal axis 100. The first drive member 35 is inserted into the second drive member 37.

During a dose set and dispense operation, the first drive member 35 is rotationally locked to the second drive member 37 by a clutch 39. In particular, at its proximal end, the first drive member 35 comprises radial teeth 355 being in a clutched engagement with matching teeth 375 on the inner surface of a flange 373 near the proximal end of the second drive member 37.

In order to maintain the clutched engagement during a dose set and dispense operation, a spring 72 is located inside the dose member 7, being compressed between an inner face at the proximal end of the dose member 7 and an outer face 358 at the proximal end of the first drive member 35. Thereby, the spring 72 exerts an axial force in the distal direction 103 on the first drive member 35, pressing the first drive member 35 towards the second drive member 37. Moreover, the dose member 7 comprises an internal boss 74 which extends in an axial direction and comes into contact with the outer face 358 of the first drive member 35 on a further compression of the spring 72.

This helps to maintain the clutched engagement in a dose dispense operation and serves as a counter-bearing for the first drive member 35 in a reset operation.

The drug delivery device 1 comprises a track 4, wherein two sets of protrusions 310, 311 on the outer surface of the second drive member 32 are guided during set and dispense operations. Thereby, the relative movement of the drive unit 3 and the main housing 21 is defined by and confined to the possible movement of the sets of protrusions 310, 311 along the track 4. In particular, the track 4 is provided by contact faces 400, 401 on the distal and proximal ends of an insert 27 fixed to the main housing 21. The insert 27 has the shape of a hollow sleeve, surrounding the second drive member 37. The first set of protrusions 310 runs along the distal contact face 400 and the second set of protrusions 311 runs along the proximal contact face 401.

The track 4 comprises several dose set 41 and dose dispense sections 42. The dose dispense sections 42 run in an axial direction, while the dose set sections 41 run helically relative to the main hosing 21. During setting a dose, each set of protrusions 310, 311 runs along a dose set section 41 of the track 4. Thereby, the set of protrusions 310, 311 and thus, also the drive unit 3, carry out a helical movement relative to the main housing 21. During dose dispense, the protrusions 310, 311 run along a dose dispense section 42 of the track 4. Thereby, the drive unit 3 carries out an axial movement in the distal direction 103.

An insert spring 46 is located at the track 4, providing feedback to a user at specific points of operation and preventing a backwards movement of a protrusion 31 of the first set of protrusions 310 on a dose dispense section 42, after a dose has been dispensed.

FIG. 1B shows a detailed view of the insert spring 46 in the device 1 after a dose has been dispensed. The insert spring 46 is rigidly mounted between the housing 21, the insert 27 and the nut 23. The insert spring 46 features radial spring surfaces 462, 464, 466, that are disposed to interfere with a protrusion 31. The insert spring 46 comprises two radial spring surfaces 462, 466 which are arranged to deflect radially when deformed by the protrusion 31 and, thereby, after the completion of a dose set and dose dispense operation provide audible and tactile feedback to the user. The spring surface 462 indicating the start of a dose set operation also stops the second drive member 37 from sliding up the dose set section 41 without user input.

Another surface 464 is arranged to provide a non-return or unidirectional feature that permits the axial travel of the protrusion 31 in the distal direction 103 but prevents a travel in the proximal direction 104. Thereby, after a dose dispense operation, a backwards movement of the protrusions 31 along a dose dispense section 42 is prevented.

Furthermore, returning to FIG. 1A, a back-off spring 26 is rigidly mounted between the nut 23 and the second drive member 37 and abuts a distal face 372 of the second drive member 37. At the end of a dose dispense operation the back-off spring 26 is compressed by the second drive member 37 such that the back-off spring 26 produces an axial counterforce on the drive member 37 in the proximal direction 104. Thereby, after a dose dispense operation a small movement of the second drive member 37 can be triggered, causing a small movement of the piston rod 5 in the proximal direction. This allows a backing-off of the bung 225 in the proximal direction 104, whereby a dripping of the medicament can be prevented after the dose has been dispensed. Moreover, the axial load produced by the back-off spring 26 leads to a small movement of the protrusion 31 in a proximal direction 104, whereby the protrusion 31 is pushed onto a tilted part of the non-return surface 464 of the insert spring 46. This results in a small rotational movement of the second drive member 37 such that the sets of protrusions 310, 311 contact the subsequent dose set section 42.

Moreover, the drug delivery device 1 comprises a last dose nut 24, threadedly engaged with a last dose thread 353 on the distal end of the first drive member 35. At its outer surface, the last dose nut 24 comprises notches 242 engaged with axial splines 232 on the nut 23. Thereby, a movement of the first drive member 35 in the dose set direction 105 will result in a movement of the last dose nut 24 along the last dose thread 353 in the proximal direction 104. When the last dose of the medicament has been dispensed, the last dose nut 24 will have reached the end of its threaded engagement with the first drive member 35. Here, the last dose nut 24 will block the first drive member 35 such that a further dose set operation is prevented.

FIG. 2A shows the drug delivery device 1 before a dose set operation.

For setting a dose, the user rotates the dose member 7 relative to the main housing 21 in the dose set direction 105. As the dose member 7 is rotationally locked to the second drive member 37 by the lugs 76 guided in the axial grooves 377 on the second drive member 37, a rotation of the dose member 7 also causes the second drive member 37 to rotate.

As the second drive member 37 rotates, one of the protrusions 31 travels underneath a detent on the insert spring 46 giving the user audible and tactile feedback, indicating that a dose set operation has started.

The two sets of protrusions 310, 311 travel along the dose set section 41 of the track 4. This results in a helical movement of the dose member 7 and the second drive member 37. Thereby, the dose member 7 comes out of the proximal end of the main housing 21. Due to the clutched engagement of the first drive member 35 and the second drive member 37 maintained by the spring 72, the first drive member 35 travels along the same helical path as the second drive member 37. The pitch of the helical dose set section 41 is identical to the pitch of the inner thread 32 at the inner face of the first drive member 35, to which the piston rod 5 is engaged. Thus, the first drive member 35 travels along its threaded engagement with the piston rod 5 without transmitting a load on the piston rod 5, whereby the piston rod 5 remains stationary.

FIG. 2B shows the drug delivery device 1 at the end of a dose set operation. Here, the dose member 7 is in a twisted-out position relative to the main housing 21. At the end of the helical dose set section 41, a protrusion 31 has traveled underneath a detent surface on the insert spring 46 giving the user feedback that a dose has been set.

During the dose set operation, the first drive member 35 has rotated relative to the last dose nut 24. Thereby, the last dose nut 24 has moved along its threaded engagement with the first drive member 35 and its splined engagement with the nut 23 in the proximal direction 104 relative to the first drive member 35.

FIG. 3 shows the dispense mechanism of the drug delivery device at the end of a dose set operation. During setting a dose, the two sets of protrusions 310, 311 have traveled along a helical dose set section 41 of the track 4. When the protrusions 310, 311 have reached the end of a dose set section 41, the first set of protrusions 310 abut stop faces 420 on the subsequent dose dispense section 42 preventing a further rotational movement in the dose set direction 105. Now, the user can choose between dispensing the dose by pushing the dose member 7 in the distal direction 103 and unsetting the dose by twisting the dose member 7 in the dose unset direction 106 opposite to the dose set direction 105.

During dose dispense, the two sets of protrusions 310, 311 run along an axial dose dispense section 42, whereby the first 35 and second drive member 37 move axially in the distal direction 103. Thereby, the threaded engagement of the first drive member 35 with the piston rod 5 causes a distal movement of the piston rod 5 through its threaded engagement with the nut 23. This axial displacement is transmitted to the bung 225 in the cartridge 224 and results in a dispense of medicament from the cartridge 224.

The differences in pitch of the thread 53 on the piston rod 5 engaged with the nut 23 and the inner thread 32 on the first drive member 35 engaged with the piston rod 5 results in a ratio reduction between the axial displacement of the piston rod 5 relative to the axial displacement of the first drive member 35 during dose dispense. Thereby, a mechanical advantage is achieved.

During dose dispense, the two sets of protrusions 310, 311 move along the dose dispense section 42 until the second set of protrusions 311 reaches a stop face 410 on a subsequent dose set section 41. Thereby, a further axial movement of the drive unit 3 in the distal direction 103 is prevented.

Furthermore, at the end of its axial travel along the track 4, a protrusion 31 on the second drive member 37 travels underneath the non-return feature of the insert spring 46. This provides feedback to the user that the dose dispense operation has been completed and ensures that the second drive member 37 cannot be pulled axially back up the dose dispense section 42 of the track 4.

FIG. 4 shows the drug delivery device 1 at the end of a dose dispense operation, before the axial load on the dose member 7 supplied by the user has been removed. Thus, the dose member 7 is still in the same position relative to the drive unit 3 as during a dose dispense operation.

During the dose dispense operation, by pushing the dose member 7 in the distal direction 103, the spring 72 is compressed, thereby pressing the first drive member 35 on the second drive member 37. If the exerted load on the dose member 7 is large enough, the spring 72 is further compressed, whereby the dose member 7 carries out a small axial movement in the distal direction 103 until the lugs 377 abut a distal stop face in the groove 377 on the second drive member 37. Thereby, the boss 74 in the dose member 7 moves towards the first drive member 35 until it contacts the proximal end face 358 of the first drive member 35 and pushes it towards the second drive member 37. Thereby, the boss 74 exerts a load in the distal direction 103 on the first drive member 35, ensuring that the clutched engagement is maintained.

At the end of the dose dispense operation, the distal face 372 of the second drive member 37 compresses the back-off spring 26. This results in a counterforce in the proximal direction 104 on the second drive member 37. When the user releases the dose member 7, the back-off spring 26 is enabled to relax and thereby pushes the protrusion 31 on the second drive member 37 towards the non-return surface 464 of the insert spring 46. Thereby, the piston rod 5 carries out a small backwards movement in the proximal direction 104, allowing a relaxation of the bung 225 in the cartridge 224.

As the non-return surface 464 does not allow a further axial movement of the protrusion 31, the force produced by the back-off spring 26 is translated into a slight rotation of the second drive member 37 along the non-return surface 464. Thereby, the protrusions 31 move from a dose dispense section 42 towards a dose set section 41 enabling the setting of the next dose.

FIG. 5 shows the drug delivery device 1 during resetting.

Here, all doses have been dispensed from the medicament cartridge 224, whereby the last dose nut 24 has traveled to the end of its threaded engagement with the first drive member 35. As a result, a further setting of a dose is prevented.

The piston rod 5 is in its most distal position relative to the main housing 21. For resetting the piston rod 5 towards its initial position, the cartridge holder has been detached from the main housing 21. Thereafter, the piston rod 5 is accessible for the user and the user can apply a load on the piston rod 5 in the proximal direction 104.

This axial load on the piston rod 5 causes an axial load on the first drive member 35 via the threaded engagement of the piston rod 5 and the first drive member 35. Both a translational and rotational movement of the second drive member 37 is prevented by the second set of protrusions 311 abutting the dose dispense sections 42 of the track 4 and by the non-return feature of the insert spring 46. Thereby, the load exerted on the first drive member 35 leads to an axial movement of the first drive member 35 relative to the second drive member 37 in the proximal direction 104, whereby the clutched engagement of the first 35 and the second drive member 37 is lost. Here, the spring 72 in the dose member 7 is compressed and a small axial movement of the dose member 7 is caused until the lug 76 contacts a proximal end face of the groove 377. The first drive member 35 moves in the proximal direction 104 relative to the second drive member 37 until the boss 74 abuts the proximal end face 358 of the first drive member 35. Then, the first drive member 35 rotates relative to the second drive member 37 allowing the retraction of the piston rod 5 into the main housing 21 through its threaded engagement with the nut 23.

Once the piston rod 5 has been fully reset, the last dose nut 24 will have reached its initial position at the distal end of the last dose thread 353 on the first drive member 35.

When the user removes the axial load on the piston rod 5, the spring 72 is allowed to relax. Thereby, it exerts an axial force in the distal direction 103 on the first drive member 35 pushing it towards the second drive member 37. In the case that the teeth 355 on the first drive member 35 are rotationally aligned with the matching teeth 375 on the second drive member 37, the clutched engagement will be re-established. In the case that the relative rotational position of the teeth 355 and matching teeth 375 do not allow a re-engagement of the clutch, the clutched engagement will be established by a small rotational movement of the dose member 7. Here, a priming operation of the device 1 may be required.

When the piston rod 5 has been reset, the cartridge holder 22 comprising a new cartridge 224 can be attached to the main housing 21. As the cartridge holder 22 is attached, the bias spring 25 is compressed, imparting an axial spring load on the cartridge 224 ensuring that it is maintained in a fully distal position within the cartridge holder 22.

Here, it has to be noted that instead of moving the piston rod manually backwards, the piston rod 5 may also be reset by fitting a new cartridge 224 to the cartridge holder 22 and attaching the cartridge 22 holder to the main housing 21. Note furthermore that, preferably, the piston rod 5 can be reset at any time when the piston rod 5 can be accessed and be pushed backwards.

FIG. 6A shows a second embodiment of a drug delivery device 1 having a drive unit 3 comprising a first drive member 35 and a second drive member 37 which are rotationally and axially locked during dose dispense and allow an unlocking for resetting the piston rod 5.

In this embodiment, the insert spring 46 has been removed and its functionality has been distributed among other parts of the drug delivery device 1. Furthermore, a dose counter 8 indicating the number of remaining doses, which equals the number of remaining dose dispense operations, has been added.

In particular, the dose counter 8 comprises a number sleeve 82, carrying markings on its outer surface. The marking representing the current filling state of the cartridge 224 is visible through an opening 214 in the main housing 21. Here, also a marking may be provided indicating that a priming operation is required after resetting the device 1 or indicating that the cartridge 224 is empty.

The number sleeve 82 is driven by a rotational movement of the piston rod 5. The number sleeve 82 has a threaded engagement with an inner body 28 fixed to the main housing 21 and a splined engagement with a collar 81. The collar 81 is coupled to the main housing 21 such that a relative translational movement between the collar 81 and the housing 21 is prevented and a relative rotational movement is allowed. The collar 81 has a splined engagement with the piston rod 5 such that when the piston rod 5 carries out a rotational movement, the collar 81 equally rotates. Due to its splined engagement with the number sleeve 82, a rotation of the piston rod 5 also causes a helical movement of the number sleeve 82 through its threaded engagement with the inner body 28. The markings on the number sleeve 82 are printed over a helical path on the outer surface of the number sleeve 82 so that after a dose dispense operation the next marking appears in the opening 214.

The pitch of the thread 83 on the number sleeve 82 engaged with the body insert 28 can be selected such that the axial advancement of the number sleeve 82 is smaller or larger than the axial advancement of the piston rod 5. This allows all the required numbers to be printed on the number sleeve 82 in a legible size and allows minimizing the length of the number sleeve 82.

The drug delivery device 1 can be reset in the same way as in the first embodiment by pushing the piston rod 5 in the proximal direction, whereby the clutch 39 between the first drive member 35 and the second driver member 37 disengages. Here, during resetting the piston rod 5 also the number sleeve 82 returns to its initial position.

Moreover, the first drive member 35 has been modified such that the last dose nut 24 abuts against a stop face 354 on the first drive member 35 at the end of its threaded engagement with the piston rod 5. Thereby, a damaging of the end of the last dose thread 353 or a bump-over of the last dose nut 24 over the end of the last dose thread 353 can be prevented.

Moreover, in this embodiment, the spring 72 in the dose member 7 abuts on a collar 357 on the first drive member 35, thereby pushing the first drive member 35 towards the second drive member 37 and maintaining their clutched engagement. The first drive member 35 extends through the spring 72 and contacts a boss 74 on the dose member 7 during a dose dispense operation and during resetting the device 1. Here, the boss 74 is a small inner protrusion on the dose member 7. Thereby, the size of the drug delivery device 1 is further reduced.

FIG. 6B shows some key features of the second drive member 37 of the drug delivery device 1 according to FIG. 6A. At its outer surface, the second drive member 37 comprises only one set of protrusions 310 guided in a track 4 for setting and dispensing doses of medicament. In this embodiment, as can be seen in FIG. 6A, the track 4 is provided by a channel formed between an inner body 28 and a body insert 27. The body insert 27 is permanently and rigidly fixed to the inner body 28. This allows a further reduction of the size of the drug delivery device 1.

Furthermore, the second drive member 37 has flexible arms 378 acting on detent features on the inner surface of the inner body 28, thereby providing user feedback at the start and the end of a dose set operation. Furthermore, the second drive member 37 has a series of helical sweep recesses 379 around its outer diameter having steps between each other. The recesses 379 interact with flexible arms on the inner body 28 providing user feedback and a non-return ratchet when the flexible arms 378 click over a step at the end of a dose dispense operation.

FIG. 7A shows a third embodiment of a drug delivery device 1 having a drive unit 3 comprising a first drive member 35 and a second drive member 37.

At its proximal end, the first drive member 35 comprises protrusions 356 being in a clutched engagement with recesses 370 on the proximal end of the second drive member 37 during a dose dispense operation, preventing a relative rotational movement between the first 35 and second drive member 37.

Also here, the drug delivery device 1 comprises a dose counter 8 comprising a number sleeve 82 being driven by a collar 81. The number sleeve 82 is threadedly engaged with an inner body 28. At its outer surface, the second drive member 37 comprises only one set of protrusions 310 being guided along a track 4 formed by a channel between an inner body 28 and a body insert 27.

On its outer surface, the second drive member 37 comprises ribs 376 for interaction with stop faces 77, 78 on the dose member 7. Thereby, a limited relative rotational movement of the dose member 7 and the second drive member 37 is allowed while a relative translational movement is prevented.

Moreover, the second drive member 37 comprises diamond-shaped protrusions 374 interacting with flexible arms on the inner body 28 providing user feedback at the end of a dose set and dispense operation and a non-return function.

In this embodiment, by the modified design of the second drive member 37, the mouldability of the second drive member 37 is improved.

FIG. 7B shows the dose member 7 of the device 1 of FIG. 7A. The dose member 7 comprises an internal boss 74 which together with a spring (not visible here) serves to maintain the clutched engagement of the first 35 and the second drive member 37. In its assembled state, the boss 74 acts on an inner face of the first drive member 35.

The dose member 7 comprises an inner tubular part 79 having bone-shaped openings 75, wherein the ribs 376 of the second drive member 37 are guided. The ribs 376 abut the radial end faces 77 of the openings 75 such that a relative rotational movement of the second drive member 37 and the dose member 7 is prevented. In an axial direction, a clearance between the axial end faces 78 of the dose member 7 and the ribs 376 allows a limited axial movement of the dose member 7 relative to the drive member 37. Thereby, unlocking of the first 35 and second drive member 37 for resetting the device 1 is enabled.

The invention is not restricted to the exemplary embodiments. Rather, the invention encompasses any new feature and also any combination of features, which in particular comprise any combination of features in the patent claims and any combination of features in the exemplary embodiments.

REFERENCE NUMERALS 1 drug delivery device
100 longitudinal axis
101 distal end
102 proximal end
103 distal direction
104 proximal direction
105 dose set direction
106 dose unset direction
2 housing
21 main housing
211 distal end of main housing
214 opening
22 cartridge holder
224 cartridge
225 bung
23 nut
232 spline
24 last dose nut
242 notch
25 cartridge bias spring
26 back-off spring
27 body insert
28 inner body
3 drive unit
31 protrusion on second drive member
310 first set of protrusions
311 second set of protrusions
32 inner thread on first drive member
35 first drive member
351 inner surface of first drive member
353 last dose thread 354 stop face on first drive member
355 teeth on first drive member
356 protrusions of clutch means
357 collar
358 outer face of first drive member
37 second drive member
370 recess
371 outer surface
372 distal face
373 flange
374 diamond-shaped protrusions
375 matching teeth
376 ribs
377 groove
378 flexible arm
379 helical sweep recess
39 clutch means
4 track at housing
400, 401 contact face
41 dose set section
410 stop face on dose set section
42 dose dispense section
420 stop face on dose dispense section
46 insert spring
5 piston rod
51 protrusions
53 thread on piston rod
55 start position
56 bearing
7 dose member
72 spring
74 boss
75 bone-shaped opening
76 lug
77, 78 stop face
79 inner tubular part
8 dose counter
81 collar
82 number sleeve
83 thread on number sleeve

The invention claimed is:

1. A drug delivery device comprising a resettable drive assembly, wherein the resettable drive assembly comprises a first drive member and a second drive member configured to form a drive unit for driving a piston rod, the piston rod being driven by the drive unit for dispensing a dose of a medicament in a dispense operation of the drug delivery device, and a clutch and spring configured to: prevent a relative rotational movement between the first drive member and the second drive member during a dose set operation, prevent a relative rotational movement of the first drive member and the second drive member during the dispense operation, and allow a relative rotational movement between the first drive member and the second drive member during a reset operation for enabling a resetting of the piston rod towards an initial position relative to the first drive member.

2. A resettable drive assembly for a drug delivery device comprising a first drive member and a second drive member configured to form a drive unit for driving a piston rod in a dispense operation of the drug delivery device, and a clutch and spring configured to: prevent a relative rotational movement between the first drive member and the second drive member during a dose set operation, prevent a relative rotational movement of the first drive member and the second drive member during the dispense operation, and allow a relative rotational movement between the first drive member and the second drive member during a reset operation for enabling a resetting of the piston rod towards an initial position relative to the first drive member.

3. The resettable drive assembly according to claim 2, wherein the clutch and spring are configured such that exerting a load onto the first drive member in a proximal direction of the drive assembly rotationally unlocks the first drive member and the second drive member for enabling the resetting of the piston rod.

4. The resettable drive assembly according to claim 2, wherein the clutch and spring are configured to exert a load onto one of the first drive member and the second drive member such that the first drive member and the second drive member are rotationally locked in the dispense operation of the drug delivery device.

5. The resettable drive assembly according to claim 2, wherein the clutch is configured to rotationally lock the first drive member and the second drive member during the dispense operation of the drug delivery device.

6. The resettable drive assembly according to claim 2, wherein the first drive member and the second drive member have the shape of sleeves, and wherein the first drive member is at least partly positioned within the second drive member.

7. A drug delivery device comprising a resettable drive assembly, wherein the resettable drive assembly comprises a first drive member and a second drive member configured to form a drive unit for driving a piston rod, the piston rod being driven by the drive unit for dispensing a dose of a medicament in a dispense operation of the drug delivery device, a clutch and spring configured to prevent a relative rotational movement of the first drive member and the second drive member during the dispense operation and configured to allow a relative rotational movement between the first drive member and the second drive member during a reset operation, and a dose member operable to control a set operation of the drug delivery device, wherein the dose member is coupled to the second drive member such that a relative rotational movement of the dose member and the second drive member is prevented, and wherein the piston rod is movable towards an initial position relative to the first drive member for resetting the drug delivery device during the reset operation.

8. The drug delivery device according to claim 7, comprising a main housing having a longitudinal axis, wherein a free rotational movement of the second drive member relative to the main housing is prevented in one rotational direction around the longitudinal axis.

9. The drug delivery device according to claim 7, being configured as a fixed-dose device.

10. The drug delivery device according to claim 7, wherein the piston rod is threadedly engaged with the first drive member.

11. The drug delivery device according to claim 7, wherein the dose member is coupled to the second drive member such that a limited axial movement between the dose member and the second drive member is enabled.

12. The drug delivery device according to claim 7, wherein the dose member is configured such that on exerting a load on the dose member in the distal direction, the dose member exerts a load onto one of the first and the second drive member, thereby rotationally locking the first and the second drive member in the dispense operation of the device.

13. The drug delivery device according to claim 7, wherein the dose member is configured to be twisted for setting a dose and pushed for dispensing the dose.

14. The drug delivery device according to claim 7, configured to be resettable by exerting a force on the piston rod towards the proximal direction of the drug delivery device, thereby enabling a rotational movement between the first drive member relative to the second drive member, moving the piston rod in the proximal direction of the drug delivery device, whereby the first drive member is rotated relative to the second drive member and then, releasing the piston rod.

15. The drug delivery device according to claim 14, configured such that after releasing the piston rod, the spring rotationally locks the first drive member and the second drive member.

* * * * *